_United States Patent_ [19]

Lenz

[11] 4,013,666
[45] Mar. 22, 1977

[54] (8α,13aβ)-8-CARBOCYCLIC/CARBOCYCLIC METHYL-5,8,13,13A-TETRAHYDRO-2,3,10,11-TETRAMETHOXY-6H-DIBENZO[a,g]QUINOLIZINES AND INTERMEDIATES THERETO

[75] Inventor: George R. Lenz, Glenview, Ill.

[73] Assignee: G. D. Searle & Co., Chicago, Ill.

[22] Filed: Mar. 15, 1976

[21] Appl. No.: 666,802

[52] U.S. Cl. .................. 260/289 C; 260/289 A; 424/258
[51] Int. Cl.$^2$ ................................ C07D 215/14
[58] Field of Search .................. 260/289 C, 289 A

[56] References Cited
UNITED STATES PATENTS

| | | | |
|---|---|---|---|
| 3,426,027 | 2/1969 | Muller et al. | 260/289 C |
| 3,835,140 | 9/1974 | Kwang et al. | 260/289 A |

_Primary Examiner_—Donald G. Daus
_Assistant Examiner_—D. B. Springer
_Attorney, Agent, or Firm_—John M. Brown; John A. Dhuey

[57] ABSTRACT

Preparation of antiarrhythmic and antifungal (8α,13aβ)-8-carbocyclic/carbocyclic methyl-5,8,13,13a-tetrahydro-2,3,10,11-tetramethoxy-6H-dibenzo[a,g]quinolizines is disclosed.

9 Claims, No Drawings

(8α,13aβ)-8-CARBOCYCLIC/CARBOCYCLIC METHYL-5,8,13,13A-TETRAHYDRO-2,3,10,11-TETRAMETHOXY-6H-DIBENZO[a,g]QUINOLIZINES AND INTERMEDIATES THERETO

This invention relates to (8α,13aβ)-8-carbocyclic/-carbocyclic methyl-5,8,13,13a-tetrahydro-2,3,10,11-tetramethoxy-6H-dibenzo[a,g]quinolizines and intermediates thereto. More particularly, this invention provides new, useful, and unobvious chemical compounds of the formula

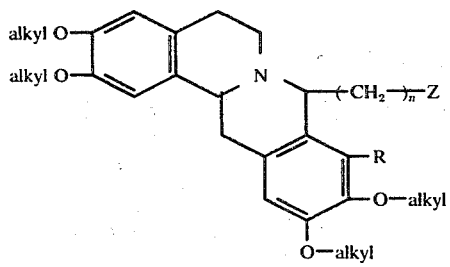

wherein Z represents a carbocyclic grouping of the formula

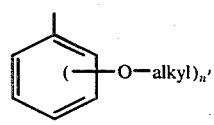

or

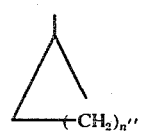

in which n' represents a positive integer less than 6 and n'' represents a positive integer less than 5, n represents 0 or 1, and R represents hydrogen or —O—alkyl.

The alkyls called for by the foregoing formulas may be alike or different, but are preferably of lower order, for example, methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, and like monovalent, saturated, acyclic, straight- or branched-chain hydrocarbon groupings of the formula

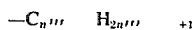

—$C_{n'''}H_{2n'''+1}$ wherein n''' represents a positive integer less than 8. Among these alkyls, methyl is especially preferred.

The number of —O—alkyl's in the aromatic carbocyclic grouping represented by Z is not critical, but fewer than 4 in positions meta and/or para to the point of attachment of Z to the remainder of the depicted molecule are preferred.

The compounds to which this invention relates are useful by reason of their valuable biological properties. Thus, for example, they are antiarrhythmic and antifungal.

In the standardized test for antiarrhythmic activity described in U.S. Pat. No. 3,905,982, the products of Examples 2C and 5C hereinafter were both active at 40 mg/L. Quinidine was likewise active in this test at 40 mg/L.

In the standardized test for antifungal activity versus *Verticillium albo-atrum* described in U.S. Pat. No. 3,652,606, the products of Examples 2C and 5C hereinafter were found to prevent the growth of this representative plant pathogen at 1000 mcg/ml.

Preparation of the compounds of this invention proceeds by contacting a 3,4-dihydroisoquinoline of the formula

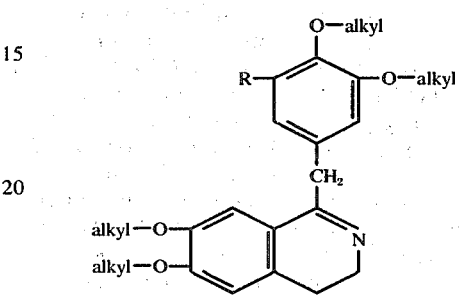

with an acid chloride or anhydride of the formulas $Z(CH_2)_nCOCl$ and $[Z(CH_2)_nCO]_2O$ respectively, in the presence of pyridine; contacting the resultant N-acyl-1,2,3,4-tetrahydroisoquinoline

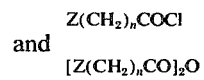

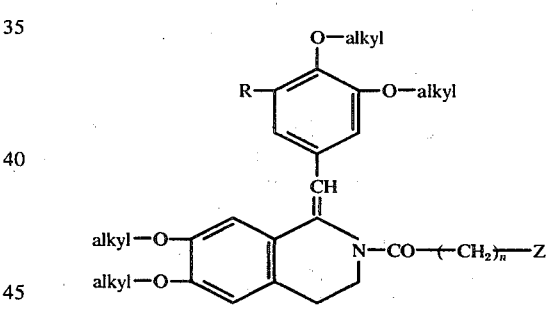

with cold concentrated sulfuric acid to effect cyclization to the corresponding 5,6-dihydrodibenzo[a,g]quinolizinium salt

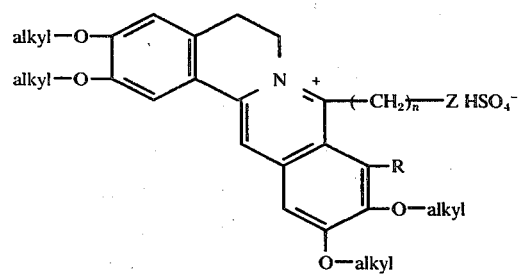

and contacting this salt with methanolic sodium tetrahydroborate(1—) — preferably, but not necessarily in the presence of aqueous alkali. Throughout the foregoing formulas, the meanings of Z, n, and R remain as originally defined.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. A suspension of 6 parts of 3,4-dihydro-6,7-dimethoxy-1-[(3,4-dimethoxyphenyl)methylene]isoquinoline (J. Chem. Soc., 1928, 501) and 6 parts of 4-methoxybenzoyl chloride in 50 parts of dry pyridine is heated at the boiling point under reflux in a nitrogen atmosphere for 45 minutes, whereupon 180 parts of chloroform is stirred in. The resultant solution is washed well with water, dried over anhydrous sodium sulfate, and stripped of solvent by vacuum distillation. The residue is (Z)-1,2,3,4-tetrahydro-6,7-dimethoxy-2-(4-methoxybenzoyl)-1-[(3,4-dimethoxyphenyl)methylene]isoquinoline, having the formula

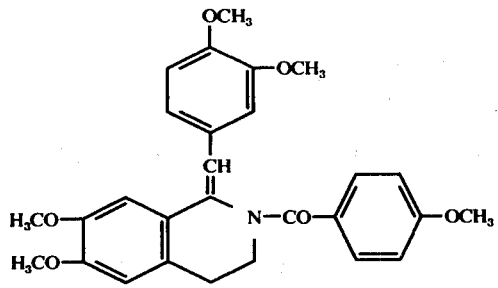

B. To 20 parts of concentrated sulfuric acid, with vigorous stirring at 0°–5°, is slowly added 1 part of (Z)-1,2,3,4-tetrahydro-6,7-dimethoxy-2-(4-methoxybenzoyl)1-[(3,4-dimethoxyphenyl)methylene]isoquinoline. Stirring is continued for approximately 2 minutes after the addition is complete, whereupon 100 parts of water is introduced and stirring then resumed for a further 5 minutes. The precipitate which forms is filtered off, washed with cold water until the washings are neutral, and dried in air, affording 5,6-dihydro-2,3,10,11-tetramethoxy-8-(4-methoxyphenyl)dibenzo[a,g]quinolizinium hydrogen sulfate, having the formula

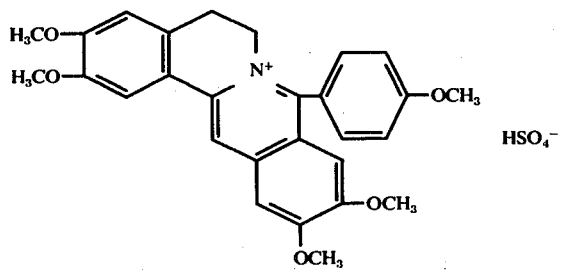

C. To a suspension of 1 part of 5,6-dihydro-2,3,10,11-tetramethoxy-8-(4-methoxyphenyl)dibenzo[a,g]quinolizinium hydrogen sulfate in 25 parts of methanol is added, with vigorous agitation, a solution of 1 part of sodium tetrahydroborate(1—) and 1 part of potassium hydroxide in 10 parts of water. The resultant mixture is stirred for 1 hour, then poured into 100 parts of water. The mixture thus obtained is extracted with dichloromethane. The dichloromethane extract is dried over anhydrous sodium sulfate and stripped of solvent by vacuum distillation. The residue is (8α,13aβ)-5,8,13,13a-tetrahydro-2,3,10,11-tetramethoxy-8-(4-methoxyphenyl)-6H-dibenzo[a,g]quinolizine, which can be further purified by recrystallization from aqueous methanol, and has the formula

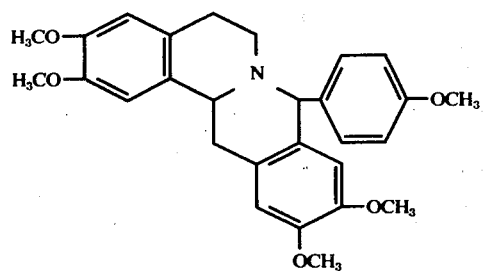

EXAMPLE 2

A. A suspension of 6 parts of 3,4-dihydro-6,7-dimethoxy-1-[(3,4-dimethoxyphenyl)methylene]isoquinoline and 6 parts of 3,4,5-trimethoxybenzoyl chloride in 50 parts of pyridine is heated at the boiling point under reflux in a nitrogen atmosphere for 45 minutes, whereupon 180 parts of chloroform is introduced. The resultant solution is washed with water, dried over anhydrous sodium sulfate, and stripped of solvent by vacuum distillation. The residue is taken up in benzene; and the benzene solution is chromatographed on silica gel, using benzene and mixtures thereof with increasing amounts of ethyl acetate as developing solvents. From an eluate comprising 30% ethyl acetate in benzene, on evaporation of solvent, (Z)-1,2,3,4-tetrahydro-6,7-dimethoxy-2-(3,4,5-trimethoxybenzoyl)-1-[(3,4-dimethoxyphenyl)methylene]isoquinoline melting at 195°–200° is obtained as the residue.

B. Substitution of 1 part of (Z)-1,2,3,4-tetrahydro-6,7-dimethoxy-2-(3,4,5-trimethoxybenzoyl)-1-[(3,4-dimethoxyphenyl)methylene]isoquinoline for the (Z)-1,2,3,4-tetrahydro-6,7-dimethoxy-2-(4-methoxybenzoyl)-1-[(3,4-dimethoxyphenyl)methylene]isoquinoline called for in Example 1B affords, by the procedure there detailed, 5,6-dihydro-2,3,10,11-tetramethoxy-8-(3,4,5-trimethoxyphenyl)dibenzo[a,g]quinolizinium hydrogen sulfate melting above 300°.

C. Substitution of 1 part of 5,6-dihydro-2,3,10,11-tetramethoxy-8-(3,4,5-trimethoxyphenyl)dibenzo[a,g-

]quinolizinium hydrogen sulfate for the 5,6-dihydro-2,3,10,11-tetramethoxy-8-(4-methoxyphenyl)dibenzo[a,g]quinolizinium hydrogen sulfate called for in Example 1C affords, by the procedure there detailed, (8α,13aβ)-5,8,13,13a-tetrahydro-2,3,10,11-tetramethoxy-8-(3,4,5-trimethoxy)-6H-dibenzo[a,g]quinolizine melting at 158°–160°.

EXAMPLE 3

A. To a suspension of 12 parts of 3,4-dihydro-6,7-dimethoxy-1-[(3,4-dimethoxyphenyl)methylene]isoquinoline in 50 parts of pyridine and 5 parts of N-ethyl-N-(1-methylethyl)-2-propanamine is added a solution of 10 parts of 3,4,5-trimethoxybenzeneacetyl chloride in 45 parts of benzene. The resultant mixture is heated at the boiling point under reflux for 1 hour, then cooled and thereupon diluted with 500 parts of chloroform. The resultant solution is washed with water, dried over anhydrous sodium sulfate, and stripped of solvent by vacuum distillation. The residue is crystallized from a mixture of ethyl acetate and ether to give (Z)-1,2,3,4-tetrahydro-6,7-dimethoxy-2-(3,4,5-trimethoxybenzeneacetyl-1-[(3,4-dimethoxyphenyl)-methylene]isoquinoline melting at 164°–170°.

B. To 10 parts of concentrated sulfuric acid, with vigorous agitation at 0°–5°, is slowly added 1 part of (Z)-1,2,3,4-tetrahydro-6,7-dimethoxy-2-(3,4,5-trimethoxybenzeneacetyl-1-[(3,4-dimethoxyphenyl)methylene]isoquinoline. When the addition is complete, 50 parts of water is introduced; and the resultant mixture is allowed to stand for 18 hours, whereupon the aqueous supernatant is decanted and the residual oil triturated with 25 parts of methanol. The bright yellow crystals which form are isolated by filtration, washed with water until the washings are neutral, and dried in air, affording 5,6-dihydro-2,3,10,11-tetramethoxy-8-[(3,4,5-trimethoxyphenyl)methyl]dibenzo[a,g]quinolizinium hydrogen sulfate melting above 300°.

C. To a suspension of 1 part of 5,6-dihydro-2,3,10,11-tetramethoxy-8-[(3,4,5-trimethoxyphenyl)methyl]dibenzo[a,g]quinolizinium hydrogen sulfate in 10 parts of methanol is added a solution of 1 part of sodium tetrahydroborate(1—) and 1 part of sodium hydroxide in 10 parts of water. The resultant mixture is stirred for 1 hour, whereupon 100 parts of water is introduced. The mixture thus obtained is extracted with dichloromethane. The dichloromethane extract is dried over anhydrous sodium sulfate and stripped of solvent by vacuum distillation. The residue is (8α,13aβ)-5,8,13,13a-tetrahydro-2,3,10,11-tetramethoxy-8-[(3,4,5-trimethoxyphenyl)methyl]-6H-dibenzo[a,g]quinolizine, which can be further purified by crystallization from aqueous methanol. The product has the formula

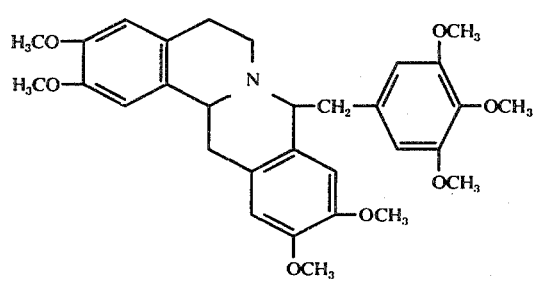

EXAMPLE 4

A. To a suspension of 24 parts of 3,4,5-trimethoxybenzeneacetic acid in 25 parts of benzene is added 7 parts of N,N-diethyl-1-propyne-1-amine, followed by a solution of 12 parts of 3,4-dihydro-6,7-dimethoxy-1-[(3,4,5-trimethoxyphenyl)methylene]isoquinoline [Ber. deut. chem. Ges., 55, 2989 (1922)] in 60 parts of pyridine. The resultant mixture is stirred at room temperatures for 18 hours, whereupon it is consecutively washed with aqueous 5% potassium carbonate, approximately 0.2% hydrochloric acid, and water, then dried over anhydrous sodium sulfate and stripped of solvent by vacuum distillation. The residue, crystallized from methanol, affords (Z)-1,2,3,4-tetrahydro-6,7-dimethoxy-2-(3,4,5-trimethoxybenzeneacetyl)-1-[(3,4,5-trimethoxyphenyl)methylene]isoquinoline melting at 148°–150°.

B. Substitution of 1 part of (Z)-1,2,3,4-tetrahydro-6,7-dimethoxy-2-(3,4,5-trimethoxybenzeneacetyl)-1-[(3,4,5-trimethoxyphenyl)methylene]isoquinoline for the (Z)-1,2,3,4-tetrahydro-6,7-dimethoxy-2-(3,4,5-trimethoxybenzeneacetyl)-1-[(3,4-dimethoxyphenyl)-methylene]isoquinoline called for in Example 3B affords, by the procedure there detailed, 5,6-dihydro-2,3,9,10,11-pentamethoxy-8-[(3,4,5-trimethoxyphenyl)methyl]dibenzo[a,g]quinolizinium hydrogen sulfate.

C. To a suspension of 1 part of 5,6-dihydro2,3,9,10,11-pentamethoxy-8-[(3,4,5-trimethoxyphenyl)methyl]dibenzo[a,g]quinolizinium hydrogen sulfate in 10 parts of methanol is added 2 parts of sodium tetrahydroborate(1—), followed by 100 parts of water. The resultant mixture is extracted with dichloromethane. The dichloromethane extract is dried over anhydrous sodium sulfate and stripped of solvent by vacuum distillation. The residue is (8α,13aβ)-5,8,13,13a-tetrahydro-2,3,9,10,11-pentamethoxy-8-[(3,4,5-trimethoxyphenyl)methyl]-6H-dibenzo[a,g]quinolizine, which can be further purified by crystallization from aqueous methanol.

EXAMPLE 5

A. To a suspension of 6 parts of 3,4-dihydro-6,7-dimethoxy-1-[(3,4-dimethoxyphenyl)methylene]isoquinoline hydrochloride in 40 parts of pyridine is added 6 parts of cyclopropanecarbonyl chloride. The resultant mixture is stirred at room temperatures for 18 hours, then poured into 500 parts of water. The mixture thus obtained is extracted with chloroform. The chloroform extract is washed with 5% hydrochloric acid, dried over anhydrous sodium sulfate, and stripped of solvent by vacuum distillation. The residue is crystallized from a mixture of ethyl acetate and dichloromethane to give (Z)-2-cyclopropylcarbonyl- 1,2,3,4-tetrahydro-6,7-dimethoxy-1-[(3,4-dimethoxyphenyl)methylene]isoquinoline melting at 148°–151°.

B. To 10 parts of concentrated sulfuric acid, with vigorous agitation at 0°, is slowly added 1 part of (Z)-2-cyclopropylcarbonyl-1,2,3,4-tetrahydro-6,7-dimethoxy1-[(3,4-dimethoxyphenyl)methylene]isoquinoline. When the addition is complete, 90 parts of water is mixed in; and the yellow precipitate which forms is isolated by filtration and recrystallized from water, affording 8-cyclopropyl5,6-dihydro-2,3,10,11-tetramethoxydibenzo[a,g]quinolizinium hydrogen sulfate melting above 300°.

C. To a rapidly-stirred solution of 1 part of 8-cyclopropyl-5,6-dihydro-2,3,10,11-tetramethoxydibenzo[a,g]quinolizinium hydrogen sulfate in 75 parts of methanol is added 3 parts of sodium tetrahydroborate(1—) and 7 parts of potassium hydroxide. Stirring is continued for 1½ hours, whereupon the reaction mixture is poured into 250 parts of water. The mixture thus obtained is extracted with dichloromethane. The dichloromethane extract is dried over anhydrous sodium sulfate and stripped of solvent by vacuum distillation. The residue, crystallized from a mixture of ethyl acetate and ether, affords (8α,13aβ)8-cyclopropyl-5,8,13,13a-tetrahydro-2,3,10,11-tetramethoxy-6H-dibenzo[a,g]quinolizine melting at 170°–172°. The product has the formula

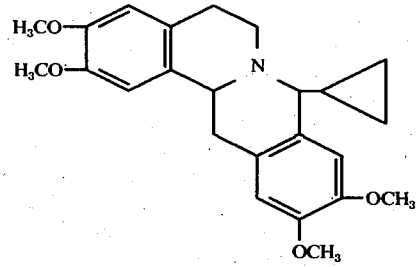

EXAMPLE 6

A. To a suspension of 5 parts of 3,4-dihydro-6,7-dimethoxy-1-[(3,4,5-trimethoxyphenyl)methylene]isoquinoline in 50 parts of pyridine is added 4 parts of cyclopropanecarbonyl chloride. The resultant mixture is stirred overnight, whereupon most of the pyridine is removed by vacuum distillation and the residue taken up in chloroform. The chloroform extract is consecutively washed with water and aqueous 5% sodium bicarbonate, then dried over anhydrous sodium sulfate, and finally stripped of solvent by vacuum distillation. The residue is (Z)-2-cyclopropanecarbonyl-1,2,3,4-tetrahydro-6,7-dimethoxy-1-[(3,4,5-trimethoxyphenyl)methylene]isoquinoline.

B. To 10 parts of concentrated sulfuric acid, with vigorous agitation at 5°–10°, is slowly added 1 part of (Z)-2-cyclopropanecarbonyl-1,2,3,4-tetrahydro-6,7-dimethoxy-1-[(3,4,5-trimethoxyphenyl)methylene]isoquinoline, followed by 100 parts of water. The yellow precipitate thrown down is isolated by filtration, washed with water until the washings are neutral, and dried in air, affording 8-cyclopropyl-5,6-dihydro-2,3,9,10,11-pentamethoxydibenzo-[a,g]quinolizinium hydrogen sulfate.

C. To a suspension of 1 part of 8-cyclopropyl-5,6-dihydro-2,3,10,11,12-pentamethoxydibenzo[a,g]quinolizinium hydrogen sulfate in 25 parts of methanol is added, with rapid stirring, a solution of 1 part of sodium tetrahydroborate(1—) and 1 part of sodium hydroxide in 10 parts of water. When the reaction mixture becomes colorless, approximately 250 parts of water is introduced; and the mixture thus obtained is extracted with dichloromethane. The dichloromethane extract is dried over anhydrous sodium sulfate and stripped of solvent by vacuum distillation. The residue is (8α,13aβ)-8-cyclopropyl-5,8,13,13a-tetrahydro-2,3,9,10,11-pentamethoxy-6H-dibenzo[a,g]quinolizine, which can be further purified by crystallization from aqueous methanol.

EXAMPLE 7

A. To a solution of 5 parts of 3,4-dihydro-6,7-dimethoxy-1-[(3,4-dimethoxyphenyl)methylene]isoquinoline in 50 parts of pyridine is added 5 parts of cyclohexanecarbonyl chloride. The resultant mixture is stirred for 18 hours, then poured into 500 parts of water. The mixture thus obtained is extracted with chloroform. The chloroform extract is washed with water, dried over anhydrous sodium sulfate, and stripped of solvent by vacuum distillation. The residue is (Z)-2-cyclohexanecarbonyl-1,2,3,4-tetrahydro-6,7-dimethoxy-1-[(3,4-dimethoxyphenyl)methylene]isoquinoline, which can be further purified by crystallization from a mixture of ethyl acetate and ether.

B. Substitution of 1 part of (Z)-2-cyclohexanecarbonyl-1,2,3,4-tetrahydro-6,7-dimethoxy-1-[(3,4-dimethoxyphenyl)methylene]isoquinoline for the (Z)-2-cyclopropanecarbonyl-1,2,3,4-tetrahydro-6,7-dimethoxy-1-[(3,4,5-trimethoxyphenyl)methylene]isoquinoline called for in Example 6B affords, by the procedure there detailed, 8-cyclohexyl-5,6-dihydro-2,3,10,11-tetramethoxydibenzo[a,g]quinolizinium hydrogen sulfate.

C. Substitution of 1 part of 8-cyclohexyl-5,6-dihydro-2,3,10,11-tetramethoxydibenzo[a,g]quinolizinium hydrogen sulfate for the 8-cyclopropyl-5,6-dihydro-2,3,9,10,11-pentamethoxydibenzo[a,g]quinolizinium hydrogen sulfate called for in Example 6C affords, by the procedure there detailed, (8α,13aβ)-8-cyclohexyl-5,8,13,13a-tetrahydro-2,3,10,11-tetramethoxy-6H-dibenzo[a,g]quinolizine.

EXAMPLE 8

A. To a suspension of 5 parts of 3,4-dihydro-6,7-dimethoxy-1-[(3,4,5-trimethoxyphenyl)methylene]isoquinoline in 50 parts of benzene is added 15 parts of pyridine, followed by 3 parts of cyclohexanecarbonyl chloride. The resultant mixture is heated at the boiling point under reflux in a nitrogen atmosphere for 2 hours, then cooled, consecutively washed with water and aqueous 5% sodium becarbonate, dried over anhydrous sodium sulfate, and stripped of solvent by vacuum distillation. The residue is crystallized from a mixture of ethyl acetate and ether to afford (Z)-2-cyclohexanecarbonyl-1,2,3,4-tetrahydro-6,7-dimethoxy-1-[(3,4,5-trimethoxyphenyl)methylene]isoquinoline melting at 162°–164°.

B. Substitution of 1 part of (Z)-2-cyclohexanecarbonyl-1,2,3,4-tetrahydro-6,7-dimethoxy-1-[(3,4,5-trimethoxyphenyl)methylene]isoquinoline for the (Z)-2-cyclopropanecarbonyl-1,2,3,4-tetrahydro-6,7-dimethoxy-1-[(3,4,5-trimethoxyphenyl)methylene]isoquinoline called for in Example 6B affords, by the procedure there detailed, 8-cyclohexyl-5,6-dihydro-2,3,9,10,11-pentamethoxydibenzo[a,g-]quinolizinium hydrogen sulfate.

C. Substitution of 1 part of 8-cyclohexyl-5,6-dihydro-2,3,9,10,11-pentamethoxydibenzo[a,g]quinolizinium hydrogen sulfate for the 8-cyclopropyl-5,6-dihydro-2,3,9,10,11-pentamethoxydibenzo[a,g]quinolizinium hydrogen sulfate called for in Example 6C affords, by the procedure there detailed (8α,13aβ)-8-cyclohexyl-5,8,13,13a-tetrahydro-2,3,9,10,11-pentamethoxy-6H-dibenzo[a,g]quinolizine.

EXAMPLE 9

A. To a mixture of 2 parts of 3,4-dihydro-6,7-dimethoxy-1-[(3,4-dimethoxyphenyl)methylene]isoquinoline, 4 parts of pyridine, and 20 parts of chloroform at 0° is added, with stirring, 3 parts of cyclohexaneacetyl chloride. The resultant mixture is stirred for 2 hours, whereupon it is washed with water, dried over anhydrous sodium sulfate, and stripped of solvent by vacuum distillation. The residue is (Z)-2-cyclohexaneacetyl-1,2,3,4-tetrahydro-6,7-dimethoxy1-[(3,4-dimethoxyphenyl)methylene]isoquinoline, which can be further purified by crystallization from a mixture of ethyl acetate and ether.

B. Substitution of 1 part of (Z)-2-cyclohexaneacetyl-1,2,3,4-tetrahydro-6,7-dimethoxy-1-[(3,4-dimethoxyphenyl)methylene]isoquinoline for the (Z)-2-cyclopropanecarbonyl-1,2,3,4-tetrahydro-6,7-dimethoxy-1-[(3,4,5-trimethoxyphenyl)methylene]isoquinoline called for in Example 6B affords, by the procedure there detailed, 8-cyclohexylmethyl-4,5-dihydro-2,3,10,11-tetramethoxydibenzo[a,g]quinolizinium hydrogen sulfate.

C. To a suspension of 1 part of 8-cyclohexylmethyl-5,6-dihydro-2,3,10,11-tetramethoxydibenzo[a,g-]quinolizinium hydrogen sulfate in 10 parts of methanol is added, portionwise with stirring, 2 parts of sodium tetrahydroborate(1—). Stirring is continued until the reaction mixture becomes colorless, at which point it is diluted with 100 parts of water. The precipitate thrown down is isolated by filtration and dried in air. The product thus isolated is (8α,13aβ)-8-cyclohexylmethyl-5,8,13,13a-tetrahydro-2,3,10,11-tetramethoxy-6H-dibenzo[a,g]quinolizine, which can be further purified by crystallization from aqueous methanol. The product has the formula

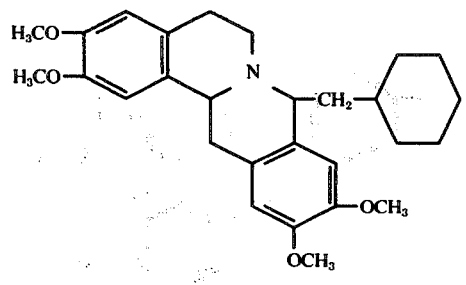

What is claimed is:
1. A compound of the formula

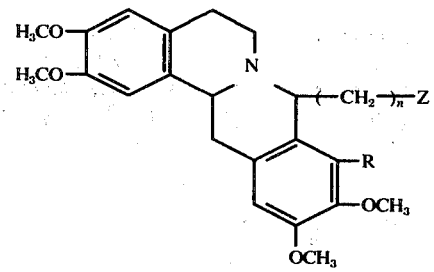

wherein Z represents (a) phenyl substituted by fewer than 4 methoxys or (b) cycloalkyl of fewer than 7 carbons, R represents hydrogen or methoxy, and n represents 0 or 1.

2. A compound according to claim 1 having the formula

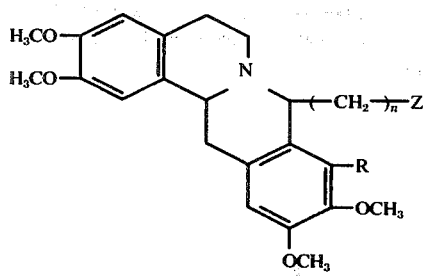

wherein Z represents phenyl substituted by fewer than 4 methoxys, R represents hydrogen or methoxy, and n represents 0 or 1.

3. A compound according to claim 1 having the formula

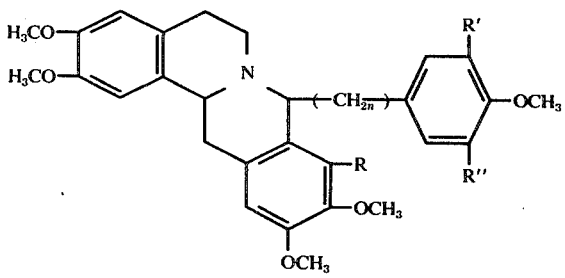

wherein R, R', and R" each represent hydrogen or methoxy and n represents 0 or 1.

4. A compound according to claim 1 having the formula

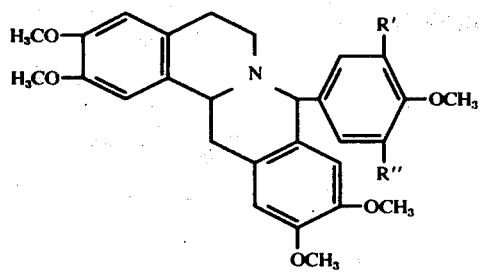

wherein R' and R" each represent hydrogen or methoxy.

5. A compound according to claim 1 which is (8α,1-3aβ)-5,8,13,13a-tetrahydro-2,3,10,11-tetramethoxy-8-(3,4,5-trimethoxyphenyl)-6H-dibenzo[a,g]quinolizine.

6. A compound according to claim 1 having the formula

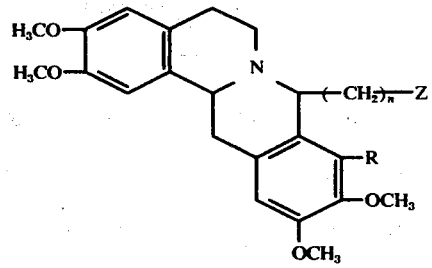

wherein Z represents cycloalkyl of fewer than 7 carbons, R represents hydrogen or methoxy, and n represents 0 or 1.

7. A compound according to claim 1 having the formula

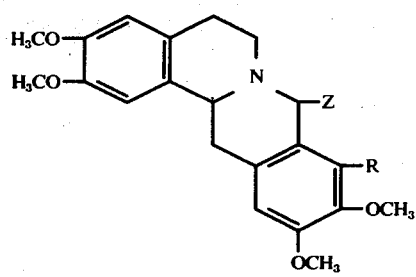

wherein Z represents cycloalkyl of fewer than 7 carbons and R represents hydrogen or methoxy.

8. A compound according to claim 1 having the formula

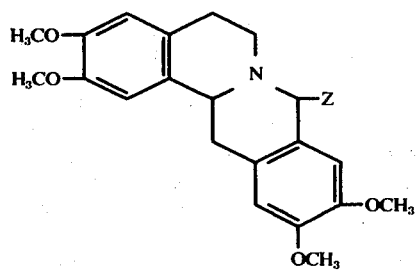

wherein Z represents cycloalkyl of fewer than 7 carbons.

9. A compound according to claim 1 which is (8α,1-3aβ)-8-cyclopropyl-5,8,13,13a-tetrahydro-2,3,10,11-tetramethoxy-6H-dibenzo[a,g]quinolizine.

* * * * *